US00PP35462P2

(12) United States Plant Patent
Hansen

(10) Patent No.: US PP35,462 P2
(45) Date of Patent: Nov. 7, 2023

(54) ***ECHINACEA* PLANT NAMED 'RAINBOW SHERBET'**

(50) Latin Name: ***Echinacea* hybrid**
Varietal Denomination: Rainbow Sherbet

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 37 days.

(21) Appl. No.: 17/803,932

(22) Filed: Jan. 26, 2023

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson

(57) ABSTRACT

The new and distinct cultivar of *Echinacea* plant named 'Rainbow Sherbet' of heavily branched plants, strong-stemmed, producing fragrant inflorescences with wide ray florets initially of orange-sherbet coloring transitioning to raspberry sherbet coloring and drooping and maturing to a light pinkish color. The center disk florets of raspberry-pink produce a large center pompon. The new plant has dark-green ovate foliage, produces flowers from mid-summer to late summer, and is suitable as a potted plant, for the landscape, and for cut flower arrangements.

2 Drawing Sheets

Botanical denomination: *Echinacea* hybrid.
Cultivar designation: 'Rainbow Sherbet'.

STATEMENT REGARDING PRIOR DISCLOSURES UNDER 37 CFR 1.77(b)(6)

The first non-enabling disclosures of the claimed plant, in the form of a photograph and brief description on a website operated by Walters Gardens, Inc. on Feb. 1, 2022, followed by a photograph and brief description in the "Walters Gardens 2022-2023 Catalog" on Jun. 8, 2022. The claimed plant was first sold on May 4, 2022, to Quality Greenhouses and Perennial Farm, Inc. by Walters Gardens, Inc., who obtained the new plant and all information relating thereto from the inventor. No plants of *Echinacea* 'Rainbow Sherbet' have been sold in this country or anywhere in the world, nor has any disclosure of the new plant been made, more than one year prior to the filing date of this application, and such sale or disclosure within one year was either derived directly or indirectly from the inventor and therefore a 35 U.S.C. §102(b) exception.

BACKGROUND OF THE INVENTION

The present invention relates to the new and distinct cultivar of Coneflower from the genus *Echinacea* and given the cultivar name 'Rainbow Sherbet'. The new plant was the result of a cross by the inventor of an unnamed proprietary hybrid known as 17-6-2 (not patented) as the female parent and an unnamed proprietary hybrid known as 17-2-3 (not patented) as the male in the summer of 2018, at a wholesale perennial nursery in Zeeland, Mich. The single seedling selected was evaluated initially in trials in the summer of 2019 at the same nursery and assigned the breeder code of 18-35-1.

*Echinacea* 'Rainbow Sherbet' has been asexually propagated at the same nursery by crown division and also using careful shoot tip tissue culture procedures and found to reproduce plants that exhibit all the characteristics identical to the original plant in successive generations.

*Echinacea* 'Rainbow Sherbet' is distinct from all other Coneflowers known to the inventor. The nearest comparison cultivars are: 'Butterfly Kisses' U.S. Plant Pat. No 24,458, 'Strawberry Mousse' (not patented), 'Razzmatazz' U.S. Plant Pat. No 13,894, 'Delicious Candy' (not patented), and 'Secret Affair' U.S. Plant Pat. No. 24,354.

'Butterfly Kisses' has a shorter habit with smaller inflorescences having light-pink ray florets and deeper pink disk florets that stay close to the same colors through maturity. 'Strawberry Mousse' is taller in habit, with inflorescences having ray florets of a lighter purplish-pink color that droop more, and the disk pompon is smaller and a lighter purplish-pink. 'Razzmatazz' is much taller in habit, has smaller inflorescences with light pinkish-purple ray florets, and a slightly darker pompom of medium purplish-pink disk florets. 'Delicious Candy' has a much shorter habit, with smaller inflorescences, the ray florets are a bright fuchsia color, and the disk florets are a reddish-orange. 'Secret Affair' has a taller and less upright habit, inflorescences with a single row of more drooping ray florets with a deeper pink, and a large pompon disk with fewer florets of deeper pink.

The female parent plant, 17-6-2, has smaller inflorescences having ray florets that begin reddish-colored and become more magenta-colored, and large disk florets of a deeper magenta color producing a pompon effect. The, male parent plant, 17-2-3, has smaller inflorescences having ray florets or near white and large disk florets of a creamy-yellow producing a pompon effect.

SUMMARY OF THE INVENTION

*Echinacea* 'Rainbow Sherbet' has not been evaluated under all possible environmental conditions. The phenotype may vary with variations in the environment including: growing temperature, available sunlight, nutrients, water, etc. without a change in the genotype of the plant. The new plant is distinct from its parents and all other *Echinacea* known to the applicant in the following combined traits:

1. Fragrant inflorescences with orange sherbet-colored ray florets;
2. Wide ray florets transition to raspberry-sherbet color and mature to a light pinkish color;
3. Very large disk florets of raspberry-pink;
4. Center pompon of disk florets that have notched apices;
5. Vigorous, compact, growth habit with heavy branching, and strong stems;
6. Dark-green ovate foliage.

BRIEF DESCRIPTION OF THE DRAWINGS

The photographs of 'Rainbow Sherbet' demonstrate the overall appearance of the plant including the unique traits. The drawings of the new plant are of a two-year-old plant grown in a full-sun trial garden in Zeeland, Mich. The colors are as accurate as reasonably possible with color reproductions. Some slight variations of color may occur as a result of lighting quality, intensity, wavelength, direction, or reflection.

DETAILED DESCRIPTION OF THE PLANT

Figure 1:
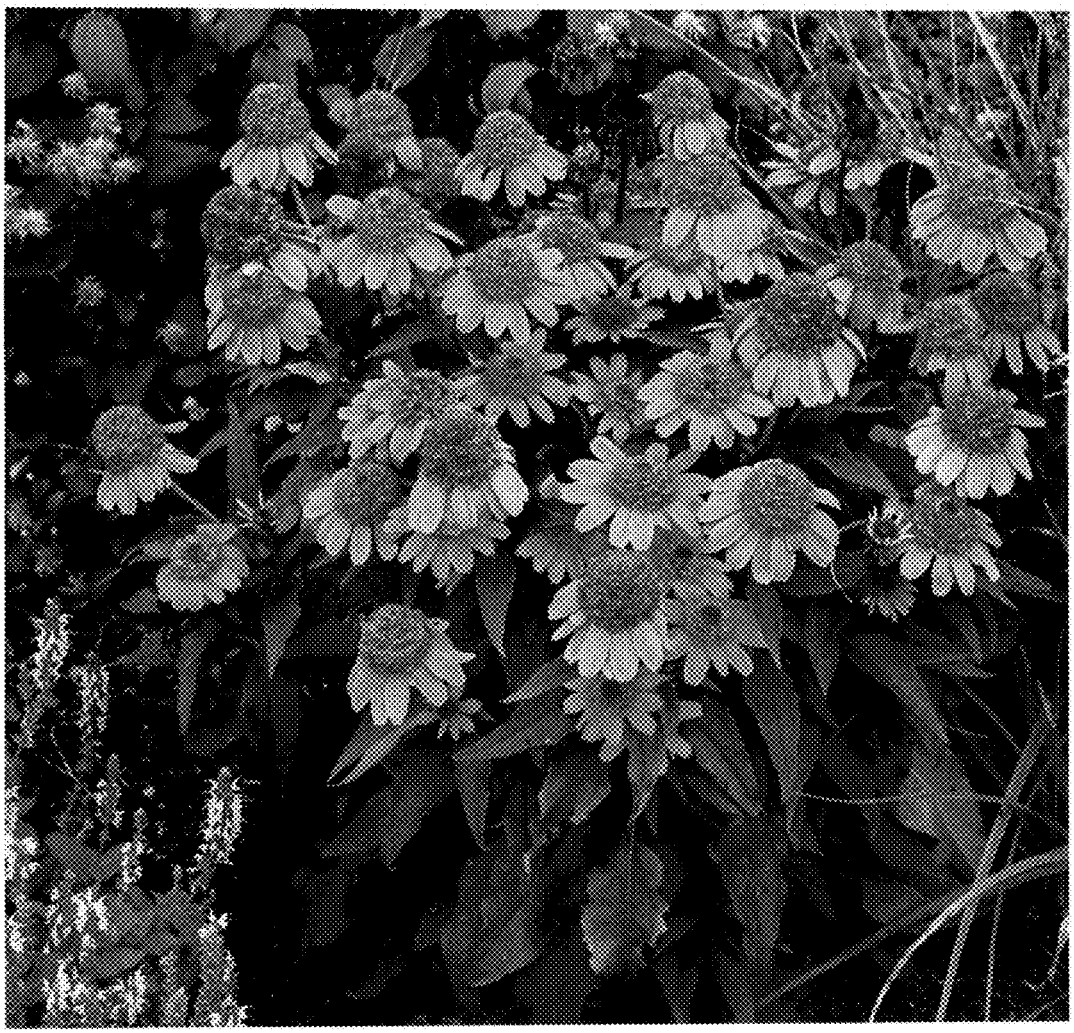
FIG. 1 shows the habit of the new plant in the flower.
Figure 2:
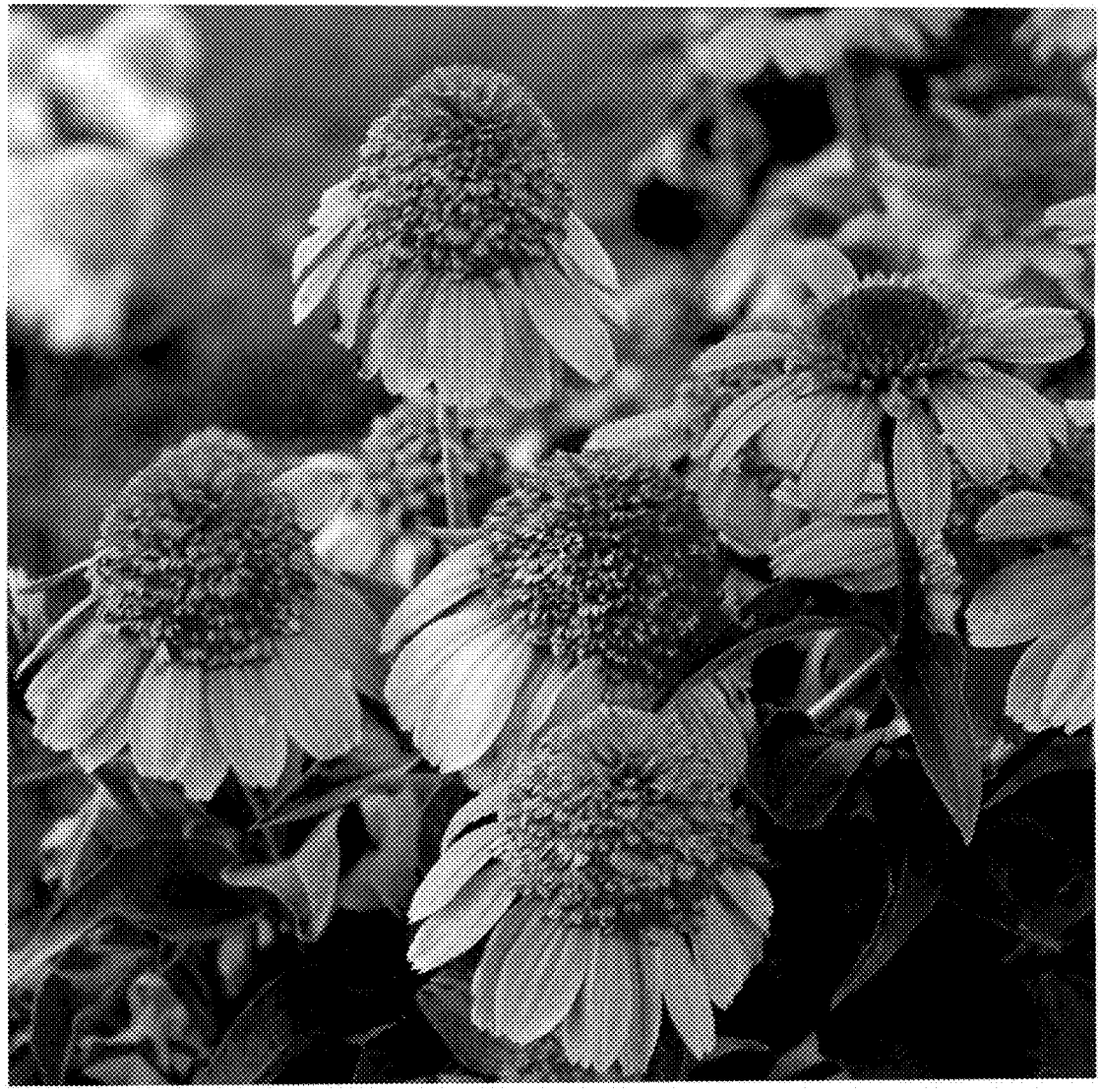
FIG. 2 shows a close-up from above of some inflorescences with flat ray florets at various stages of color and large center pompon.

The following description of *Echinacea* 'Rainbow Sherbet' is based on observations of two-year-old specimens grown in a partially-shaded greenhouse and in a full-sun trial garden in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 17-6-2 comprising a complex cross with 'Solar Flare' U.S. Plant Pat. No 22,133, 'Little Annie' (not patented), 'Julia' U.S. Plant Pat. No. 24,629, 'Cleopatra' U.S. Plant Pat. No. 24,631, and 'Butterfly Kisses' U.S. Plant Pat. No 24,458; and male parent is the proprietary unreleased hybrid 17-2-3 comprising a complex crossing with offspring from 'Julia', 'Solar Flare', 'Little Annie', 'Green Jewel' U.S. Plant Pat. No. 18,678, and 'Butterfly Kisses';

Plant habit: Multi-stemmed, freely-branched, hardy herbaceous perennial, flowering to about 54 cm tall and 45 cm wide with foliage to 40 cm tall and 44 cm wide;

Growth rate: Vigorous, finishing in 4-liter containers in about 2 months during the summer;

Roots: Cream-colored, finely-branched;

Foliage: Alternate; ovate; acute apex; cuneate base; margin micro-ciliolate and serrulate with teeth to about 2 mm long and 2 mm wide; hirsutulous adaxial and abaxial; to about 14 cm long and 6 cm wide decreasing distally, average about 11 cm long and 4.5 cm wide;

Leaf color: Young leaves adaxial nearest RHS 137B, abaxial between RHS 146A and RHS 138A; mature leaves adaxial between RHS 139A and RHS NN137A, abaxial between RHS 137B and RHS 147B; variegation absent;

Foliage fragrance: Not observed;

Venation: Pinnately three-nerved; abaxial midrib and veins costate; glabrous adaxial, hirsutulous abaxial;

Vein color: Adaxial basal midrib and basal primary veins between RHS 193A and RHS 145C, distally between RHS NN137D and RHS 138A; abaxial midrib and primary veins between RHS 147C and RHS 146D, secondary veins between RHS 138A and RHS NN137D;

Petiole: Concavo-convex; glabrous adaxial; hirsutulous abaxial; to about 8.5 cm long and 9 mm wide at the semi-clasping base and 3 mm wide in middle of lowest leaves, decreasing to nearly sessile distally;

Petiole color: Adaxial center between RHS 193A and RHS 145C, margin between RHS 139A and RHS NN137A; abaxial center between RHS 147C and RHS 146D, edge nearest RHS NN37C;

Stem: Hirsutulous; cylindrical, fistulous; strong; stiff; to about 50 cm long including peduncle and about 8 mm diameter at base; average 48 cm long and 7 mm diameter; about 9 per plant; aspect upright;

Stem color: Nearest RHS 146C;

Peduncle: Hirsutulous to pubescent; terete; strong; stiff; branched; about 13 cm long and 5 mm diameter above last leaves; quantity per stem about four to six; aspect ascending;

Peduncle color: Proximally nearest RHS 146C;

Internode: 9 to 11 per stem; average about 4.5 cm long, shorter proximally and longer distally; node color same as surrounding peduncle;

Branches: Cylindrical; hirsutulous; tightly angled to main stem to about 60° above horizontal: about 3 to 5 branches per stem; to about 26 cm long and 4.5 mm diameter;

Branch color: Proximally nearest RHS 146C;

Inflorescence: Bracteate head, aggregate of achene; with single whorl of distinct ligulate ray florets and enlarged disk florets above pappus producing a pompon effect; flowering mid-summer to late summer; initial inflorescence largest, to about 11 cm wide, with inner pompon to 5 cm across and 4.5 cm tall; to 4 to 6 inflorescences per stem;

Inflorescence fragrance: Faint, lightly sweet, honey-like;

Flower persistence: Remaining effective in color for 10 to 14 days depending on temperatures, cone drying on the plant, and effective into winter;

Involucre: With numerous bracts, about 50 to 60 per inflorescence in 3 to 4 whorls; arcuate downward toward peduncle;

Involucre bracts: Deltoid; acute apex; truncate base; ciliolate margin; reflexed; adaxial glabrous to micro-puberulent; abaxial hirsutulous; to about 11 mm long and 3 mm across decreasing distally; color adaxial center nearest RHS 138A, adaxial edges between RHS NN137C and RHS 137B, and abaxial nearest RHS 138A;

Inflorescence buds with ray florets vertical and still enrolled: About 30 mm across and 25 mm tall; ray floret adaxial color between RHS 18A and RHS 16B, abaxial color nearest RHS 16C with slight blush of nearest RHS 166D, disk florets nearest RHS 145B, and spines nearest RHS 166D distally and nearest RHS 145A proximally; disk florets to about 12 mm long, 3 mm wide at apex, and 1.5 mm wide at base; disk floret bud color nearest RHS 187C distally and transitioning to nearest RHS 145D proximally;

Ray florets: Ligulate; zygomorphic; arrangement in a single whorl, slightly to moderately imbricate when horizontal and becoming more imbricate when drooping; apex emarginated with two notches to 2 mm deep; base attenuate; margin entire; adaxial and abaxial surfaces matte; 16 to 22 per inflorescence; opening to horizontal, drooping up to 45 degrees below horizontal with maturity; flat, twisting absent; sterile; ray floret to 44 mm long and 16 mm wide near middle, base 2.5 mm wide; average size 42 mm long, 14 mm wide at center tapering to 2 mm wide at base; adaxial veins thickened and slightly sulcate;

Ray floret color: Changing with maturity; when first horizontal young adaxial nearest RHS 172B, abaxial between RHS 59B and RHS 59C; when first horizontal adaxial nearest RHS 33C, abaxial nearest RHS 33D; in mid-open period adaxial between RHS 70C and RHS 63B, abaxial nearest RHS 51D; before dropping adaxial between RHS 54D and RHS 62D, abaxial nearest RHS 65C; basal 2 mm remaining constant between RHS 146D and RHS 145A in both adaxial and abaxial;

Disk florets: About 400 to 500 per inflorescence; zygomorphic; perfect; produced in a large raised dome about 5 cm across and 4.5 cm tall; individually to about 27 mm long, 7 mm across at apex, and 1 mm diameter at base;

*Disk floret corolla.*—Typically five tepals fused forming tube; to about 17 mm long and 7 mm wide at apex, fused in tube in basal 13 mm, free in distal 4 mm; individual tepals about 2 mm wide at fusion; acute apex; entire margin; both surfaces slightly lustrous.

*Disk floret corolla tube color.*—Initially upon first opening adaxial and abaxial between RHS 43C and RHS 44D with base between RHS 162D and RHS 145C; in maturity adaxial and abaxial between RHS 63C and RHS 63B distally with base nearest RHS 145C.

*Androecium.*—Present on disk florets only; five; synandrous.

*Staminal column.*—About 0.7 mm wide, about 4 mm long and not exserted; five fused stamens.

*Anthers.*—Fused, about 2 mm long and 0.7 mm diameter; color nearest RHS N199A.

*Filaments.*—Five; attached to column; thin, less than 0.2 mm diameter and 2 mm long; color nearest RHS 200D.

*Pollen.*—Not observed.

*Gynoecium.*—On ray and disk florets; single; to 5 mm long.

*Style.*—Cylindrical; to about 4 mm long and 0.2 mm diameter; color nearest RHS 200A.

*Stigma.*—Bifid; about 1 mm long and 0.1 mm diameter; color nearest RHS 200A.

*Ovary.*—Inferior; obdeltoid; to 2 mm long and 1.5 mm wide at apex; color between RHS 161D and RHS 158D.

*Fruit.*—Not yet observed.

Receptacle spines: With disk florets; acicular; narrowly acute apex; glabrous; lustrous; to 13 mm long and 2 mm across near middle; producing a cone about 35 mm wide and 25 mm tall;

Spine color: Adaxial and abaxial apices or distal 2 mm nearest RHS 187A, middle portion nearest RHS 146C, proximal portion nearest RHS 155C;

Disease resistance: Resistance and susceptibility beyond that of other hardy Coneflower cultivars have not been observed;

Growth: The plant grows best with plenty of moisture and adequate drainage but is able to tolerate some drought when mature;

Winter hardiness: At least from USDA zone 4 through 8.

I claim:

1. A new and distinct cultivar of *Echinacea* plant named 'Rainbow Sherbet' as herein described and illustrated.

* * * * *